US008952214B2

United States Patent
Boucher, Jr. et al.

(10) Patent No.: US 8,952,214 B2
(45) Date of Patent: Feb. 10, 2015

(54) ANIMAL MODEL FOR CHRONIC OBSTRUCTIVE PULMONARY DISEASE AND CYSTIC FIBROSIS

(75) Inventors: Richard C. Boucher, Jr., Chapel Hill, NC (US); Wanda O'Neal, Cary, NC (US); Barbara Grubb, Hillsborough, NC (US); Marcus Mall, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 960 days.

(21) Appl. No.: 12/823,243

(22) Filed: Jun. 25, 2010

(65) Prior Publication Data

US 2010/0263064 A1 Oct. 14, 2010

Related U.S. Application Data

(63) Continuation of application No. 12/233,869, filed on Sep. 19, 2008, now Pat. No. 7,772,458, which is a continuation of application No. 10/448,784, filed on May 30, 2003, now Pat. No. 7,514,593.

(51) Int. Cl.
*A01K 67/027* (2006.01)
(52) U.S. Cl.
USPC ................................................. 800/18; 800/8
(58) Field of Classification Search
USPC ....................................................... 800/8, 18
See application file for complete search history.

(56) References Cited

U.S. PATENT DOCUMENTS

| | | | |
|---|---|---|---|
| 4,736,866 | A | 4/1988 | Leder et al. |
| 4,761,371 | A | 8/1988 | Bell et al. |
| 4,873,191 | A | 10/1989 | Wagner et al. |
| 4,877,729 | A | 10/1989 | Clark et al. |
| 4,879,224 | A | 11/1989 | Wallner et al. |
| 4,912,038 | A | 3/1990 | Schilling, Jr. et al. |
| 5,573,933 | A | 11/1996 | Seamark et al. |
| 5,589,604 | A | 12/1996 | Drohan et al. |
| 5,602,306 | A | 2/1997 | Townes et al. |
| 5,625,124 | A | 4/1997 | Falk et al. |
| 5,639,457 | A | 6/1997 | Brem et al. |
| 5,639,940 | A | 6/1997 | Garner et al. |
| 5,709,844 | A | 1/1998 | Arbeit et al. |
| 5,859,310 | A | 1/1999 | Bujard et al. |
| 5,880,327 | A | 3/1999 | Lubon et al. |
| 5,959,171 | A | 9/1999 | Hyttinen et al. |
| 6,166,288 | A | 12/2000 | Diamond et al. |
| 6,204,431 | B1 | 3/2001 | Prieto et al. |
| 6,255,554 | B1 | 7/2001 | Lubon et al. |
| 6,331,658 | B1 | 12/2001 | Cooper et al. |
| 6,339,183 | B1 | 1/2002 | Sun |
| 6,344,596 | B1 | 2/2002 | Velander et al. |
| 6,369,294 | B1 | 4/2002 | Piedrahita et al. |
| 6,448,469 | B1 | 9/2002 | Smith |
| 6,743,966 | B2 | 6/2004 | Smith |
| 6,891,081 | B1 | 5/2005 | Stern et al. |
| 7,045,677 | B2 | 5/2006 | Cottingham |

FOREIGN PATENT DOCUMENTS

| | | |
|---|---|---|
| WO | WO 94/12649 A2 | 6/1994 |
| WO | WO 01/64717 A1 | 9/2001 |
| WO | WO 02/094876 A2 | 11/2002 |

OTHER PUBLICATIONS

Cowan (Xenotransplantation, 2003, vol. 10, p. 223-231).*
Wall (1996, Theriogenology, vol. 45, p. 57-68).*
Ebert (1988, Mol. Endocrinology, vol. 2, pp. 277-283).*
Mullins (1990, Nature, vol. 344, p. 541-544).*
Hammer (1990, Cell, vol. 63, p. 1099-1112).*
Mullins, 1989, EMBO, vol. 8, p. 4065-4072.*
Taurog, 1988, J. Immunol., vol. 141, p. 4020-4023.*
MGI Mammalian Phenotype Browser for "Impaired mucociliary clearance", 2013.*
Hammer RE et al. Genetic engineering of mammalian embryos. J. Anim. Sci. 1986; 63: 269-278.
Hammer RE et al. Spontaneous inflammatory disease in transgenic rats expressing HLA-B27 and Human $\beta_2$m: an animal model of HLA-B27-associated human disorders. Cell. Nov. 30, 1990: 1099-1112.
Cowan PJ et al. Targeting gene expression to endothelium in transgenic animals: a comparison of the human ICAM-2, PECAM-1 and endolin promoters. Xenotransplantation. 2001; 10: 223-231.
Vaisman BL et al. ABCA1 overexpression leads to hyperalphalipoproteinemia and increased biliary cholesterol excretion in transgenic mice. The Journal of Clinical Investigation. Jul. 2001; 108(2): 303-309.
Tamba K et al. Epithelial sodium channels expressed in *Xenopus* oocytes are activated by cyclic-AMP. Clin Exp Nephrol 2002; 6: 195-201.
Yan W et al. Cystic fibrosis transmembrane conductance regulator differentially regulates human and mouse epithelial sodium channels in *Xenopus* oocytes. The Journal of Biological Chemistry. May 28, 2004; 270(22): 23183-23192.
Frizzell R A and Pilewski J M. Finally, mice with CF lung disease. Nature Medicine (May 2004), vol. 10, No. 5, pp. 452-454.
Mall M et al. Increased airway epithelial Na$^+$ absorption produces cystic fibrosis-like lung disease in mice. Nature Medicine. (May 2004), vol. 10, No. 5, pp. 487-493.

(Continued)

*Primary Examiner* — Michael C. Wilson
(74) *Attorney, Agent, or Firm* — Myers Bigel Sibley & Sajovec, P.A.

(57) ABSTRACT

A nonhuman transgenic mammal is described whose genome comprises a promoter construct operably linked to a heterologous DNA encoding an epithelial sodium channel β subunit, wherein said promoter construct directs expression of the epithelial sodium channel β subunit in lung epithelial cells of said animal, and wherein said transgenic mammal has increased lung mucus retention as compared to the corresponding wild-type mammal. The animal is useful in screening compounds for activity in treating lung diseases such as cystic fibrosis and chronic obstructive pulmonary disease.

10 Claims, 11 Drawing Sheets

(56) References Cited

OTHER PUBLICATIONS

Canessa et al. (1994), "Membrane topology of the epithelial sodium channel in intact cells," Am. J. Physiol. 267: C1682-C1690.
Schild et al. (1997), "Identification of amino acid residues in the α, β, and γ subunits of the epithelial sodium channel (ENaC) involved in amiloride block and ion permeation," J. Gen. Physiol. 109: 15-26.
Mano and Driscoll (1999), "DEG/ENaC channels: a touchy superfamily that watches its salt," BioEssays 21: 568-578.
Benos and Stanton (1999), "Functional domains within the degenerin/epithelial sodium channel (Deg/ENaC) superfamily of ion channels," J. Physiol. 520,3: 631-644.
McDonald et al. (1995), "Cloning and expression of the β- and γ-subunits of the human epithelial sodium channel" Am. J. Physiol. 268: C1157-C1163.
Altschul et al. (1997), *Gapped BLAST and PSI-BLAST: a new generation of protein database search programs*, Nucleic Acids Res. 25:3389-3402.
Schaffer et al. (2001), *Improving the accuracy of PSI-BLAST protein database searches with composition-based statistics and other refinements*, Nucleic Acids Res. 29:2994-3005.
Navab, R. et al. (2002) Regulation of Human Clara Cell 10 kD Protein Expression by Chicken Ovalbumin Upstream Promoter transcription Factors (COUP-TF's). *Am. J. Respir. Cell Mol. Biol.* 27, pp. 273-285.
Ahn et al., *Cloning and Functional Expression of the Mouse Epithelial Sodium Channel*, Am. J. Physiol., vol. 277, 1999, pp. F121-F129.
Brody et al., *Structural Characterization of the Mouse Hfh4 Gene, a Developmentally Regulated Forkhead Family Member*, Genomics, vol. 45, 1992, pp. 509-518.
Canessa et al., *Amiloride-Sensitive Epithelial Na+ Channel Is Made of Three Homologous Subunits*, Nature, No. 367, 1994, pp. 463-467.
Canessa et al., *Epithelial Sodium Channel Related to Proteins Involved in Neurodegeneration*, Nature, vol. 361, 1993, pp. 467-470.
Celli, *Pulmonary Rehabilitation in Patients With COPD*, Am. J. Respir. Crit. Care Med., vol. 152, No. 3, Sep. 1995, pp. 861-864.
Chow et al., *Development of an Epithelium-Specific Expression Cassette With Human DNA Regulatory Elements for Transgene Expression in Lung Airways*, Proc. Natl. Acad. Sci. USA, vol. 94, Dec. 1997, pp. 14695-14700.
Deng et al., *Location of Crossovers During Gene Targeting With Insertion and Replacement Vectors*, Mol. Cell Biol., vol. 13, No. 4, Apr. 1993, pp. 2134-2140.
Deng et al., *Reexamination of Gene Targeting Frequency As a Function of the Extent of Homology Between the Targeting Vector and the Target Locus*, Mol., Cell Biol., vol. 12, No. 8, Aug. 1992, pp. 3365-3371.
Drazen et al., *Animal Models of Asthma and Chronic Bronchitis*, Clinical & Experimental Allergy, vol. 29, No. s2, Jun. 1999, pp. 37-47.

Glasser et al., *Genetic Element From Human Surfactant Protein SP-C Gene Confers Bronchiolar-Alveolar Cell Specificity in Transgenic Mice*, Am. J. Physiol., vol. 261, No. 4, Part 1, Oct. 1991, pp. L349-L356.
Gossler et al., *Transgenesis by Means of Blastocyst-Derived Embrionic Stem Cell Lines*, Proc. Natl. Acad. Sci. USA, vol. 83, Dec. 1986, pp. 9065-9069.
Grubb et al., *Pathophysiology of Gene-Targeted Mouse Models for Cystic Fibrosis*, Physiological Reviews, vol. 79, Suppl., No. 1, Jan. 1999, pp. S193-S214.
Hackett et al., *5'Flanking Region of the Clara Cell Secretory Protein Gene Specifies a Unique Temporal and Spatial Pattern of Gene Expression of the Developing Pulmonary Epithelium*, Am. J. Respir. Cell Mol. Biol., vol. 11, No. 2, Aug. 1994, pp. 123-129.
Hackett et al., *Cell-Specific Expression of a Clara Cell Secretory Protein-Human Growth Hormone Gene in the Bronchiolar Epithelium of Transgenic Mice*, Proc. Natl. Acad. Sci. USA, vol. 89, Oct. 1992, pp. 9079-9083.
Hagen et al., *Tissue-Specific Expression, Hormonal Regulation and 5'-Flanking Gene Region of the Rat Clara Cell 10 kDa protein: Comparison to Rabbit Uteroglobin*, Nucleic Acids Res., vol. 18, No. 10, May 25, 1990, pp. 2939-2946.
Hummler et al., *A Mouse Model for the Renal Salt-Wasting Syndrome Pseudohypoaldosteronism*, Proc. Natl. Acad. Sci. USA, vol. 94, Oct. 1997, pp. 11710-11715.
Hummler et al., *Scnn1 Sodium Channel Gene Family in Genetically Engineered Mice*, J. Am. Soc. Nephrol., vol. 11, 2000, pp. S129-S134.
Kellenberger et al., *Epithelial Sodium Channel/Degenerin Family of Ion Channels: A Variety of Functions for a Shared Structure*, Physiol. Rev., vol. 82, 2001, pp. 735-767.
Knowles et al., *Abnormal Ion Permeation Through Cystic Fibrosis Respiratory Epithelium*, Science, vol. 221, Sep. 9, 1983, pp. 1067-1069.
Knowles et al., *Abnormal Respiratory Epithelial Ion Transport in Cystic Fibrosis*, Clin. Chest Med., vol. 7, No. 2, Jun. 1986, pp. 285-297.
Knowles et al., *Relative Ion Permeability of Normal and Cystic Fibrosis Nasal Epithelium*, J. Clin. Invest., vol. 71, May 1983, pp. 1410-1417.
Thomas et al., *High-Fidelity Gene Targeting in Embryonic Stem Cells by Using Sequence Replacement Vectors*, Mol. Cell Biol., vol. 12, No. 7, Jul. 1992, pp. 2919-2923.
Voilley et al., *Cloning, Chromosomal Localization, and Physical Linkage of the β and γ Subunits (SCNN1B and SCNN1G) of the Human Epithelial Amiloride-Sensitive Sodium Channel*, Genomics, vol. 28, 1995, pp. 560-565.
Voilley et al., *The Lung Amiloride-Sensitive Na+ Channel: Biophysical Properties, Pharmacology, Ontogenesis, and Molecular Cloning*, Proc. Natl. Acad. Sci. USA, vol. 91, Jan. 1994, pp. 247-251.
Wood, *Phenotype Assessment: Are You Missing Something?*, Comparative Medicine, vol. 50, No. 1, Feb. 2000, pp. 12-15.

* cited by examiner

FIG. 7A
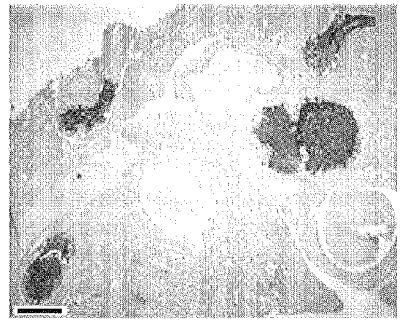
FIG. 7B
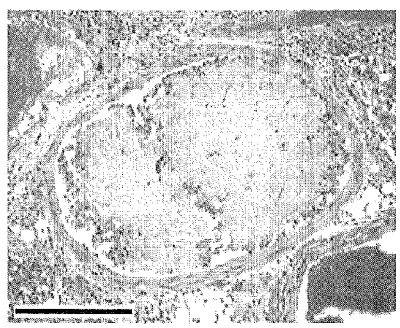
FIG. 7C
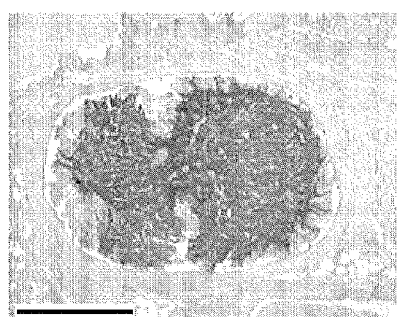
FIG. 7D
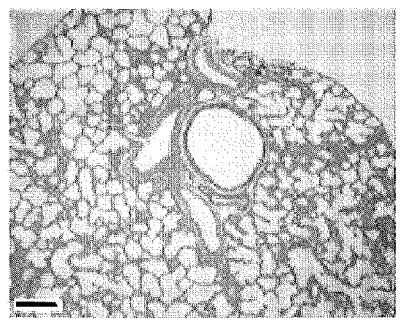
FIG. $8A_i$
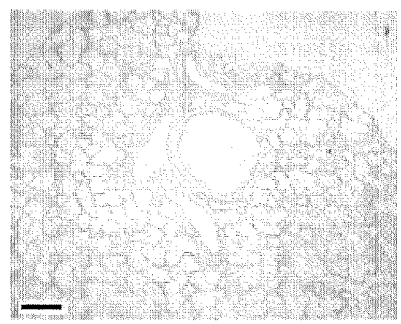
FIG. $8A_{ii}$
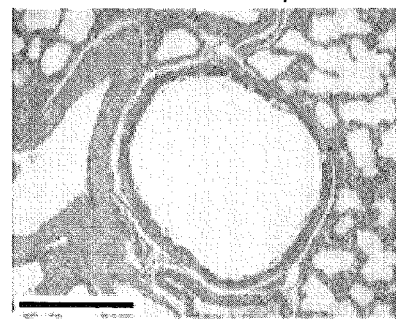
FIG. $8B_i$
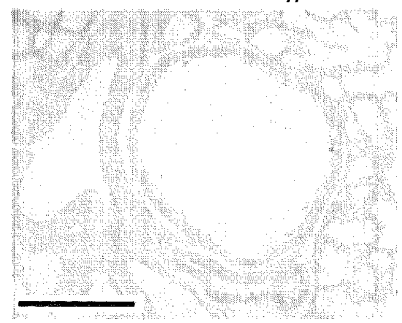
FIG. $8B_{ii}$

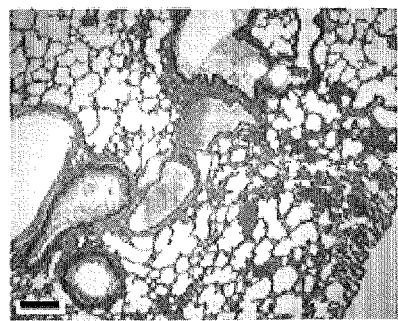
FIG. 8C$_i$
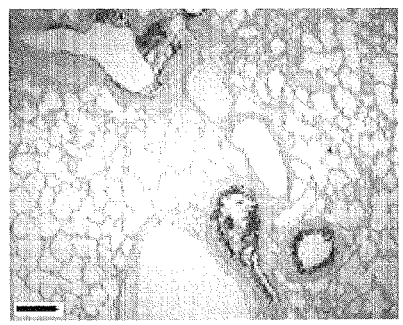
FIG. 8C$_{ii}$
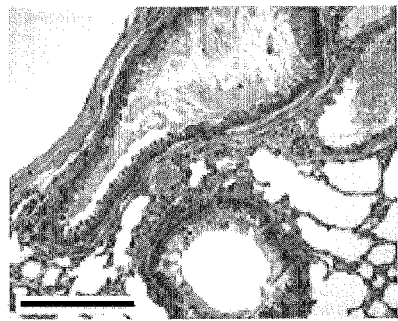
FIG. 8D$_i$
FIG. 8D$_{ii}$
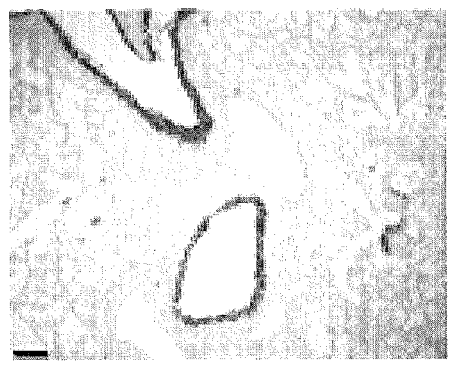
FIG. 9

ANIMAL MODEL FOR CHRONIC OBSTRUCTIVE PULMONARY DISEASE AND CYSTIC FIBROSIS

RELATED APPLICATIONS

This application claims priority to and is a continuation of U.S. patent application Ser. No. 12/233,869, filed Sep. 19, 2008, now U.S. Pat. No. 7,772,458, which is a continuation of U.S. patent application Ser. No. 10/448,784, filed May 30, 2003, now U.S. Pat. No. 7,514,593, the disclosure of each of which is incorporated by reference herein in its entirety.

STATEMENT OF FEDERAL SUPPORT

This invention was made with Government support under grant numbers HL 34322 and P50 HL60280 from the National Institutes of Health. The Government has certain rights to this invention.

FIELD OF THE INVENTION

The present invention concerns non-human transgenic animals that are useful as models of lung diseases such as chronic obstructive pulmonary disease (COPD) and cystic fibrosis.

BACKGROUND OF THE INVENTION

Cystic fibrosis (CF) is among the most prevalent, lethal diseases of genetic origin. Approximately 30,000 children and adults are affected in the United States alone. In this disease, abnormal ion transport across the respiratory epithelia leads to dehydrated, viscous and poorly-cleared airway secretions that contribute to chronic infection of the airways and early death. Knowles, *Clin. Chest. Med.* 11, 75 (1986). Chronic obstructive pulmonary disease (COPD) affects 10 to 14 million individuals in the United States and is also characterized by mucus accumulation in airway lumens and metaplasia of mucus secreting goblet cells. See, e.g. Celli et al., *Am J Respir Crit Care Med* 152, S177-S210 (1995). Hence, there is a need to develop new ways to treat cystic fibrosis and chronic obstructive pulmonary disease.

In cystic fibrosis several functions of airway epithelia are abnormal, and deficiencies in both transport $Cl^-$ and $Na^+$ absorption are well documented. See, e.g. Knowles et al., *Science* 221, 1067 (1983); Knowles et al., *J. Clint. Invest.* 71, 1410 (1983). It would be extremely useful to provide a mouse model of cystic fibrosis and chronic obstructive pulmonary disease so that treatment options to improve mucus clearance in vivo could be more vigorously pursued. Unfortunately, prior efforts to develop a mouse model of cystic fibrosis produced animals that did not develop spontaneous lung disease. See, e.g., B. Grubb and R. Boucher, *Physiological Reviews* 79, S193-S214 (1999). Accordingly, there is a need for new approaches to solving the problem of providing an animal model for cystic fibrosis or chronic obstructive pulmonary disease.

SUMMARY OF THE INVENTION

A first aspect of the present invention is a recombinant nucleic acid comprising a promoter operably linked to a heterologous nucleic acid (such as a DNA or RNA) encoding an epithelial sodium channel α subunit, β subunit, and/or γ subunit, wherein the promoter construct directs expression of the epithelial sodium channel α subunit, β subunit, and/or γ subunit in lung epithelial cells. In one preferred embodiment, the heterologous nucleic acid encodes an ENaC β subunit and directs expression of that subunit in lung epithelial cells.

A second aspect of the present invention is a host cell (particularly a mammalian host cell) containing a recombinant nucleic acid as described above.

A third aspect of the present invention is a method of making a non-human transgenic animal, comprising introducing a nucleic acid as described above into an egg cell or embryonic cell of a non-human embryo, implanting said egg or embryonic cell into a compatible female host, and raising said egg or embryonic cell to viability in said female host.

A further aspect of the present invention is a nonhuman transgenic mammal (e.g., mouse, rat, pig, monkey) whose genome comprises a promoter construct operably linked to a heterologous DNA encoding an epithelial sodium channel β subunit, wherein the promoter construct directs expression of the epithelial sodium channel β subunit in lung epithelial cells of the mammal, and wherein the transgenic mammal has increased lung mucus retention as compared to the corresponding wild-type mammal.

In one embodiment of the foregoing, the genome of the mammal preferably comprises a promoter construct operably linked to a heterologous DNA encoding an epithelial sodium channel β subunit, wherein the promoter construct directs expression of the epithelial sodium channel β subunit in lung epithelial cells of the mammal.

In one embodiment of the foregoing, the genome of the mammal further comprises a promoter construct operably linked to a heterologous DNA encoding an epithelial sodium channel α subunit, wherein the promoter construct directs expression of the epithelial sodium channel α subunit in lung epithelial cells of the mammal.

In another embodiment of the foregoing, the genome of the mammal further comprises a promoter construct operably linked to a heterologous DNA encoding an epithelial sodium channel γ subunit, wherein the promoter construct directs expression of the epithelial sodium channel γ subunit in lung epithelial cells of the mammal.

In some preferred embodiments, the nonhuman transgenic mammal has increased lung mucus plugging as compared to the corresponding wild-type (e.g., non-transformed) mammal, and/or increased mortality at 30 days of age as compared to the corresponding wild-type mammal, and/or exhibits a cystic fibrosis or chronic obstructive pulmonary disease phenotype not exhibited by the corresponding wild-type mammal.

BRIEF DESCRIPTION OF THE DRAWINGS

FIG. 7. Lung histology of a β mENaC transgene positive mouse that died spontaneously on day 20. H&E staining shows occlusion of airways throughout the lung (a,c). Scale bars=200 mm.

FIG. 8. Lung histology of β mENaC transgene positive mice that were euthanized at 3 (a,b) and 28 (c,d) days of age. All scale bars=200 mm.

FIG. 9. Lung histology of a βtg mouse that was euthanized on day 28. Scale bar=200 mm.

DETAILED DESCRIPTION OF THE PREFERRED EMBODIMENTS

Figure 1:
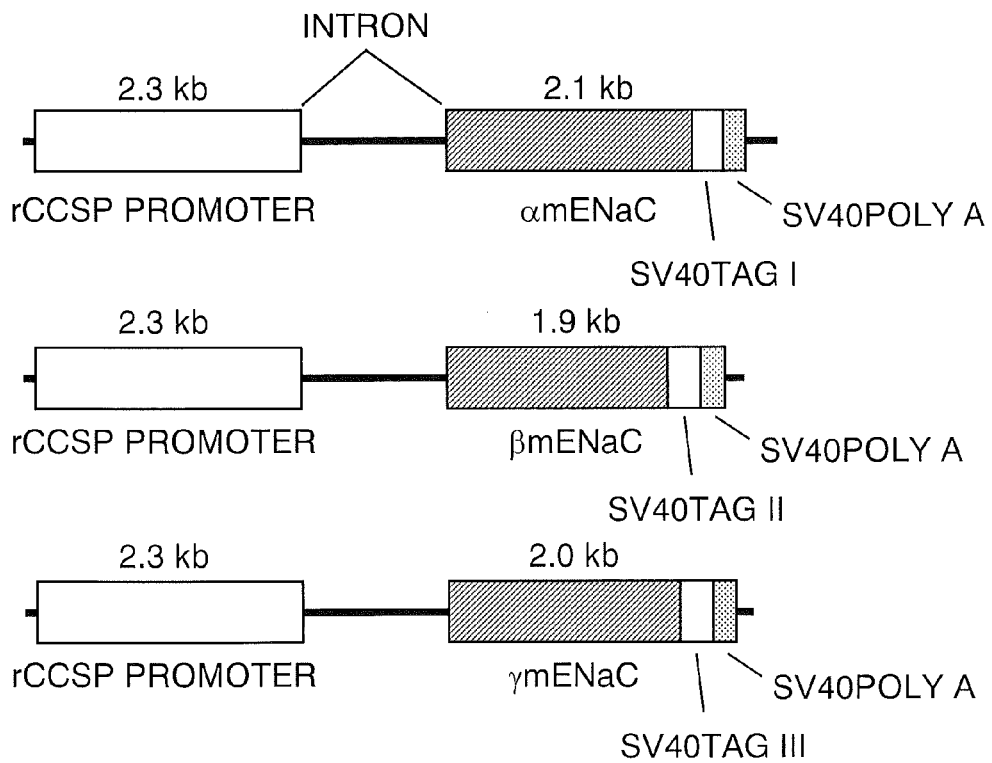
FIG. 1: Transgenic constructs for airway specific overexpression of α, β and γ mENaC.

"Mammal" as used herein refers to non-human mammals such as mice, sheep, pigs, rats, and cows.

"Operatively associated" or "operatively linked" as used herein with respect to nucleic acids indicates that the two segments of a nucleic acid functionally interact with one another in their intended manner in a host cell. For example, a promoter is operatively associated with a nucleic acid of interest when it facilitates or permits the transcription of the nucleic acid in a host cell; a locus control region is operatively associated with a promoter when it enhances the activity of the promoter to provide high level nucleic acid transcription in specific tissues, (i.e., tissue-specific expression of the associated nucleic acid).

"Epithelium sodium channel" or "ENaC" as used herein, may be of any source, including but not limited to human, mouse, rat, or other mammalian source. The epithelium sodium channel α, β, and γ subunits and nucleic acids encoding the same are known. The mouse alpha ENaC subunit is described at GENBANK Accession No. AF112185; the mouse beta ENaC subunit is described at GENBANK Accession No. NM_011325; the mouse gamma ENaC subunit is described at GENBANK Accession No. NM_011326; the rat alpha ENaC subunit is described at GENBANK Accession No. X70497; the rat beta ENaC subunit is described at GENBANK Accession No. X77932; the rat gamma ENaC subunit is described at GENBANK Accession No. X77933; the human alpha ENaC subunit is described at GENBANK Accession No. NM_001038; the, human beta ENaC subunit is described at GENBANK Accession No. NM_000336; and the human gamma ENaC subunit is described at GENBANK Accession No. NM_001039, the disclosures of all of which are incorporated by reference herein in their entirety. In addition, all 3 ENaC subunits in human and rat are described in C. Canessa et al., *Epithelial sodium channel related to proteins involved in neurodegeneration*, Nature 361 (6411), 467-470 (1993); C. Canessa et al., *Amiloride-sensitive epithelial Na+channel is made of three homologous subunits*, Nature 367 (6462), 463-467 (1994); N. Voilley et al., *The lung amiloride-sensitive Na+channel: biophysical properties, pharmacology, ontogenesis, and molecular cloning*, Proc. Natl. Acad. Sci. U.S.A. 91 (1), 247-251 (1994); N. Voilley et al., *Cloning, chromosomal localization, and physical linkage of the beta and gamma subunits (SCNN1B and SCNN1G) of the human epithelial amiloride-sensitive sodium channel*, Genomics 28 (3), 560-565 (1995), the disclosures of all of which are incorporated herein by reference in their entirety.

"Promoter" as used herein refers to any type of promoter, including constitutive promoters or regulated promoters, unless otherwise specified. Preferably the promoter is one which selectively or preferentially directs expression of the epithelial sodium channel β subunit in lung epithelial cells (e.g., a promoter that is airway cell specific, ciliated cells specific or Clara cell specific). Examples of such promoters include, but are not limited to, the Clara cell secretory protein (CCSP) promoter, the surfactant protein C promoter (S. Glasser et al., *Genetic element from human surfactant protein SP-C gene confers bronchiolar-alveolar cell specificity in transgenic mice*, Am. J. Physiol. 261, L349-L356 (1991)), the cytokeratin 18 promoter (GENBANK Accession No. AF179904 M24842 M19353 X12799; Y. Chow et al., *Development of an epithelium-specific expression cassette with human DNA regulatory elements for transgene expression in lung airways*, Proc Natl Acad Sci U S A 1997 Dec. 23; 94(26):14695-700), and the human forkhead homologue 4 promoter (S. Brody et al., *Structural characterization of the mouse Hfh4 gene, a developmentally regulated forkhead family member*, Genomics 45(3):509-18 (1997)). Such promoters may be of any source, including but not limited to human, mouse, rat, rabbit, primate or other mammalian source. The rat CCSP promoter is currently preferred and is described in GENBANK Accession No. X51318 (G. Hagen et al., *Tissue-specific expression, hormonal regulation and 5'-flanking gene region of the rat Clara cell 10 kDa protein: comparison to rabbit uteroglobin*, Nucleic Acids Res. 18 (10), 2939-2946 (1990); B. Hackett and J. Gitlin, *5' flanking region of the Clara cell secretory protein gene specifies a unique temporal and spatial pattern of gene expression in the developing pulmonary epithelium*, Am J Respir Cell Mol Biol. 11(2):123-9 (1994).

"Host cell" as used herein refers to any type of cell into which a recombinant or heterologous nucleic acid as described herein has been inserted. Such cells are generally eukaryotic cells, particularly mammalian cells, including pig, cow, sheep, and mouse cells.

"Increased lung mucus retention" as used herein is defined or characterized by the spontaneous presence of airway mucus in amounts that are readily detected by light microscopy after staining for acid and neutral mucins (e.g. with Alcian Blue and Periodic Acid Schiff staining) in transgenic animals. In contrast, wild-type animals produce only very scant spontaneous airway mucus that is not substantially detected by light microscopy.

"Increased mucus plugging" as used herein is defined or characterized by spontaneous formation of complete (plugs) or partial (plaques) obstruction of airway lumens with mucus in transgenic animals. Increased inflammation may accompany increased mucus plugging. Spontaneous mucus plug formation does not appreciably occur in wild-type animals.

"Increased mortality" as used herein is defined or characterized by an increase in death rates of transgenic animals between birth and adulthood compared to wild-type littermates. Spontaneous mortality in wild type mice in the first 8 weeks of life does not exceed ~10%. In contrast, mortality rates of different β-ENaC overexpressing mice representing certain embodiments of the present invention were ≥30%.

"Cystic fibrosis and chronic obstructive pulmonary disease phenotype" as used herein is defined as spontaneous mucus accumulation and goblet cell metaplasia, leading to the formation of mucus plugs and plaques, which in turn results in airway obstruction (e.g., as found or seen in chronic bronchitis and asthma).

The disclosures of all United States patent references cited herein are to be incorporated by reference herein in their entirety.

1. Nucleic Acid Constructs and Transformed Host Cells.

The production of recombinant nucleic acids, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

As noted above, a further aspect of the present invention is an isolated nucleic acid construct comprising at least one locus control region as described above operatively associated with a promoter. The promoter may be a heterologous promoter or homologous promoter, and where a homologous promoter the isolated nucleic acid may or may not include intervening segments.

A vector is a replicable nucleic acid construct or a nucleic acid construct used to insert particular nucleic acid constructs into a host cell. Vectors are used herein either to amplify nucleic acid constructs of the present invention or insert the constructs into a host cell or animal. Vectors comprise plasmids, viruses (e.g., adenovirus, cytomegalovirus, retroviruses), phage, and linear nucleic acids such as integratable DNA fragments (i.e., fragments integratable into the host genome by recombination). The vector may replicate and function independently of the host genome or may in some instances, integrate into the genome itself.

If desired, the vector may optionally contain flanking nucleic sequences that direct site-specific homologous recombination. The use of flanking DNA sequence to permit homologous recombination into a desired genetic locus is known in the art. At present it is preferred that up to several kilobases or more of flanking DNA corresponding to the chromosomal insertion site be present in the vector on both sides of the encoding sequence (or any other sequence of this invention to be inserted into a chromosomal location by homologous recombination) to assure precise replacement of chromosomal sequences with the exogenous DNA. See e.g. Deng et al, 1993, Mol. Cell. Biol 13(4):2134-40; Deng et al, 1992, Mol Cell Biol 12(8):3365-71; and Thomas et al, 1992, Mol Cell Biol 12(7):2919-23. It should also be noted that the cell of this invention may contain multiple copies of the gene of interest.

Transformed host cells are cells which have been transformed or transfected with vectors containing nucleic acid constructs of the invention and may or may not transcribe or translate the operatively associated nucleic acid of interest.

2. Transgenic Animals and Methods of Making.

The production of transgenic animals is well known and can be carried out in accordance with known techniques or variations thereof which will be apparent to those skilled in the art, for example as disclosed in: U.S. Pat. No. 6,344,596 to W. Velander et al. (American Red Cross); U.S. Pat. No. 6,339,183 to T. T. Sun (New York University); U.S. Pat. No. 6,331,658 to D. Cooper and E. Koren; U.S. Pat. No. 6,255,554 to H. Lubon et al. (American National Red Cross; Virginia Polytechnic Institute); U.S. Pat. No. 6,204,431 to P. Prieto et al. (Abbott Laboratories); U.S. Pat. No. 6,166,288 to L. Diamond et al. (Nextran Inc., Princeton, N.J.); U.S. Pat. No. 5,959,171 to. J. M. Hyttinin et al. (Pharming BV); U.S. Pat. No. 5,880,327 to H. Lubon et al. (American Red Cross); U.S. Pat. No. 5,639,457 to G. Brem; U.S. Pat. No. 5,639,940 to I. Garner et al. (Pharmaceutical Proteins Ltd.; Zymogenetics Inc); U.S. Pat. No. 5,589,604 to W. Drohan et al. (American Red Cross); U.S. Pat. No. 5,602,306 to Townes et al. (UAB Research Foundation); U.S. Pat. No. 4,736,866 to Leder and Stewart (Harvard); and U.S. Pat. No. 4,873,316 to Meade and Lonberg (Biogen).

For example, animals may be produced as described in U.S. Pat. No. 5,859,310 to Bujard et al., at column 17, which generally describes methods in which a transgenic animal which contains in its genome the nucleic acid of interest is produced by the following steps: (1) A chimeric DNA sequence is prepared where a Tc responsive promoter element, (comprising at least one tet operator and a minimal promoter) is cloned 5' of the DNA sequences encoding the endogenous gene of interest. (2) The chimeric DNA sequence (called also "the chimeric transgene") is then injected into a fertilized egg, which is implanted into a pseudopregnant recipient mother and allowed to develop into an adult animal. In particular, a few hundred DNA molecules are injected into the pro-nucleus of a fertilized one cell egg. The microinjected eggs are then transferred into the oviducts of pseudopregnant foster mothers and allowed to develop. See generally Brinster et al. Proc. Natl. Acad. Sci. U.S.A. Vol. 83:9065-9069 (1986). Breeding of animals resulting from this process produces offspring containing the chimeric transgene. As will be appreciated, the particular breeding strategy depends on factors such as the nucleic acid of interest and the animal into which it is inserted. Animals of the present invention can be produced by substantially the same techniques, by injecting nucleic acid constructs of the present invention.

U.S. Pat No. 4,873,191 to Wagner and Hoppe (Ohio University) describes a method of obtaining a mammal characterized as having a plurality of cells containing exogenous genetic material, the material including at least one gene and a control sequence operably associated therewith, which, under predetermined conditions, expresses the gene under the control of the control sequence in a cell of the mammal. The method, which may also be used to make animals of the present invention, comprises: (a) introducing exogenous genetic material into a pronucleus of a mammalian zygote by microinjection, the zygote being capable of development into a mammal, the genetic material including at least one gene and a control sequence operably associated therewith, thereby obtaining a genetically transformed zygote; (b) transplanting an embryo derived from the genetically transformed zygote into a pseudopregnant female capable of bearing the embryo to term; and (c) allowing the embryo to develop to term; where the gene and control sequence are selected so that the gene is not activated in such manner and degree as would prevent normal development of the embryo to term. Again, animals of the present invention can be produced by substantially the same techniques, by introducing nucleic acid constructs of the present invention into the pronucleus zygote by microinjection.

U.S. Pat. No. 6,369,294 to J. Piedrahata and F. Bazer (Texas A&M University System) describes a method of producing a transgenic pig that may be used to carry out the present invention. The method comprises (a) introducing a selected DNA segment into a cell culture comprising porcine primordial germ cells to obtain candidate porcine primordial germ cells that contain the selected DNA segment; (b) plating the candidate porcine primordial germ cells that contain the selected DNA segment on feeder cells (the feeder cells preferably at a density of between about $2.5 \times 10^5$ cells/cm$^2$ and about $10^6$ cells/m$^2$), in a culture medium comprising an effective amount of basic fibroblast growth factor and an apoptosis inhibitor, to obtain undifferentiated porcine primordial germ cells that contain the selected DNA segment; and (c) generating a transgenic pig from the undifferentiated porcine primordial germ cells that contain the selected DNA segment, wherein the selected DNA segment is contained and expressed in somatic and germ cells of the transgenic pig. Animals of the present invention can be produced in like manner by utilizing the nucleic acid constructs described herein as the selected DNA segment.

U.S. Pat. No. 5,573,933 to R. Seamark and J. Wells (Luminis Pty., Ltd.) describes a method for preparing a transgenic pig that may be used to carry out the present invention. The method comprises introducing a plasmid expression vector or a linerized insert therefrom comprising the first, second and third DNA sequences into the male pronucleus of the fertilized pig ovum prior to fusion with the female nucleus to form a single cell embryo; and, subsequently implanting the ovum into a female pig and allowing the embryo, resulting from introduction of the plasmid cloning vector into the ovum, to develop to maturity. Animals of the present invention can be produced in like manner as described therein.

3. Applications of the Invention.

The present invention provides a method of screening compounds for activity in treating lung disease. The method comprises the steps of: providing a nonhuman transgenic mammal as described herein; administering a test compound to the subject, and determining the effect of the test compound on susceptibility to airway disease in the animal, a decrease in susceptibility to airway disease in the animal indicating that the test compound may be useful in treating lung disease. The test compound may be administered by any suitable technique, including but not limited to aerosol administration, parenteral administration (subcutaneous injection, intramuscular injection, intravenous injection, etc.), transdermal administration, etc. Decrease in susceptibility to airway disease in the animal may be determined directly or indirectly by any suitable technique, including but not limited to examining any of the phenotypes exhibited by the transgenic animal as described above and examining the animal for an improvement in such phenotypes (e.g., a partial or complete return to the phenotype exhibited by the corresponding wild-type animal).

Such screens may be utilized for screening for compounds beneficial in treating any type of lung disease, particularly chronic obstructive pulmonary disease or cystic fibrosis. Any category of compound may be screened, examples including but not limited to antibiotics, osmolites, sodium channel blockers, $P2Y_2$ receptor agonists, ENaC regulators including CAP-1 protease, anti-inflammatory compounds including non-steroidal anti-inflammatory compounds, agents blocking goblet cell metaplasia and mucus hypersecretion such as epithelial growth factor (EGFR) blockers, IL-13 and IL-13 receptor blockers, blockers of the STAT6 signalling pathway, and Lomucin (produced by Genera, Research Triangle Park North Carolina, USA), anti-mucus secretion compounds such as MARCKS protein (Biomarcks, RTP), $P2Y_2$-receptor antagonists, mucolytic agents such as N-acetyl-cystein and derivatives thereof, etc.

Animals of the present invention are also useful for the identification of genes associated with airway inflammation and goblet cell metaplasia.

The present invention is explained in greater detail in the following non-limiting Examples.

EXAMPLE 1

Preparation of Transgenic Mice

Transgenic constructs for airway specific overexpression of α, β and γ mENaC. are schematically illustrated in FIG. 1. Transgenic mouse lines overexpressing α-, β-, or γ-ENaC under the control of the CCSP promoter were produced as follows: To generate plasmids for individual ENaC subunits we made use of pTG1 plasmid (obtained from Dr. Randy Thresher, Animal Model Core facility, UNC) containing two multiple cloning sites (MCS1 and MCS2), separated by an intron, and followed by a SV40 polyadenylation signal.

The rat CCSP promoter (rCCSP) was obtained from Dr. J D Gitlin J D (for reference see: Hackett B P and Gitlin J D. *Cell-specific expression of a Clara cell secretory protein-human growth hormone gene in the bronchiolar epithelium of transgenic mice*. Proc Natl Acad Sci U S A 1992 Oct. 1; 89(19):9079-83), amplified from plasmid by PCR, and cloned into MCS1 of pTG1.

ENaC subunits from mouse (α-, β-, γ-mENaC) were obtained from Dr. Tomas Kleyman (for reference see: Ahn Y J, Brooker D R, Kosari F, Harte B J, Li J, Mackler S A, Kleyman T R. *Cloning and functional expression of the mouse epithelial sodium channel*. Am J Physiol 1999 July; 277(1 Pt 2):F121-9), amplified from plasmid by PCR, and the coding sequences of individual subunits (α, β, or γ-ENaC) were cloned into MCS2 of pTG1/CCSP, respectively.

The α-construct contained nucleotides 6 to 2131 of GENBANK Accession No. AF112185 (mouse alpha ENaC subunit); the β-construct contained nucleotides 30 to 1952 of GENBANK Accession No. NM_011325 (mouse beta ENaC subunit); and the γ-construct contained nucleotides 70 to 2037 of GENBANK Accession No. NM_011326 (mouse gamma ENaC subunit). Note that constructs containing more of the untranslated sequences are expected to work equally well, as long as they contain the complete or sufficient coding sequence.

Three unique SV40 sequences of ~280 by in length were generated by PCR from pUCSV40-B2E plasmid (purchased from American Type Culture Collection, ATCC, manassas, Va.), and inserted into transgenic constructs at the 3' end of individual ENaC subunits, respectively, for purposes of detection of transgene mRNA expression (SV40tag I-III). Sequences of rCCSP, α-, β-, γ-mENaC and SV40tag I-III were verified by automatic sequencing. Individual transgenic constructs were isolated by restriction enzyme digestion, purified and injected into fertilized eggs by means of pronuclear injection (performed by Dr. Randy Thresher, Animal Model Core facility, UNC). After DNA injection, fertilized eggs were implanted into pseudopregnant recipient mothers. Animals generated by this process were genotyped to identify transgene positive founders and individual lines of transgenics were bred from these founders.

EXAMPLE 2

Detection of Transgenes in Transgenic Mice

Figure 2:
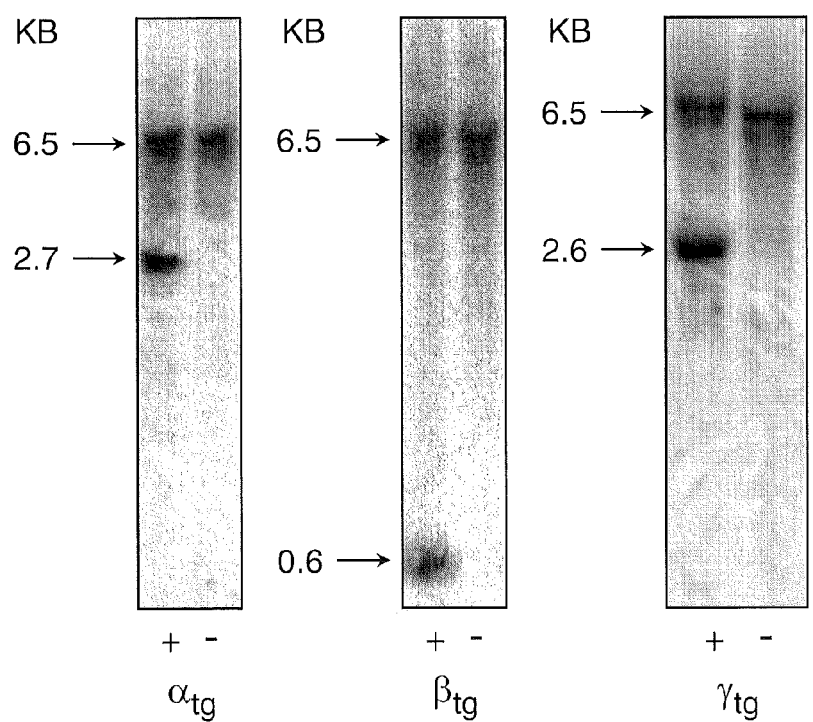
FIG. 2. Detection of α, β and γ mENaC transgenes by Southern blotting.

The detection of α, β and γ mENaC transgenes by Southern blotting is shown in FIG. 2. Transgenic (Tg) positive mice were identified by hybridization with $P^{32}$-labeled transgene-specific probes, resulting in a 2.7 kb band for αtg, a 0.6 kb band for βtg and a 2.6 kb band for γtg.

Figure 3:
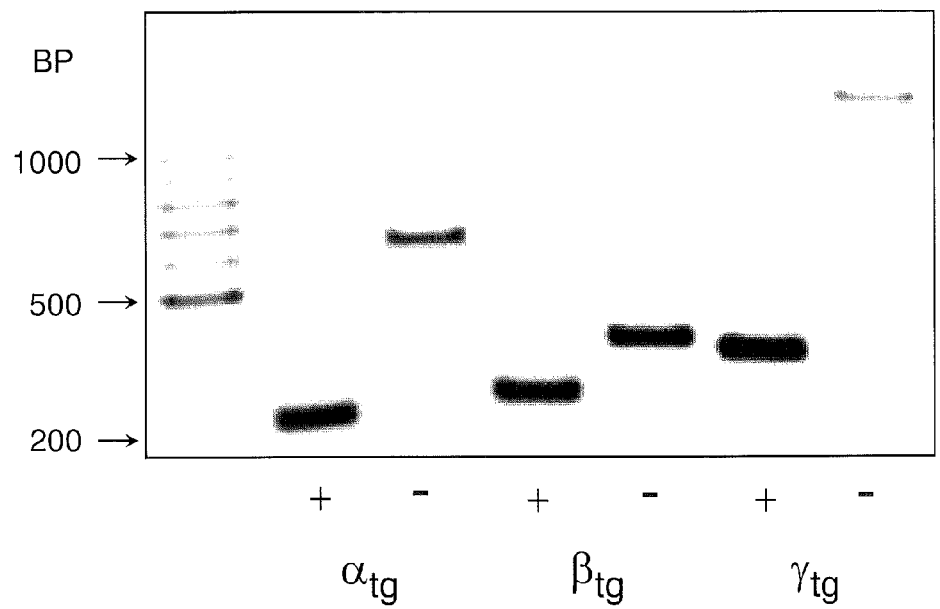
FIG. 3. Detection of α, β and γ mENaC transgenes by PCR from genomic tail DNA.

The detection of α, β and γ mENaC transgenes by PCR from genomic tail DNA is shown in FIG. 3. Length of different PCR products: αtg 228 by vs αwt ~650 bp; βtg 255 by vs βwt ~350 bp; γtg 334 by vs γwt 1200 bp.

Figure 4:
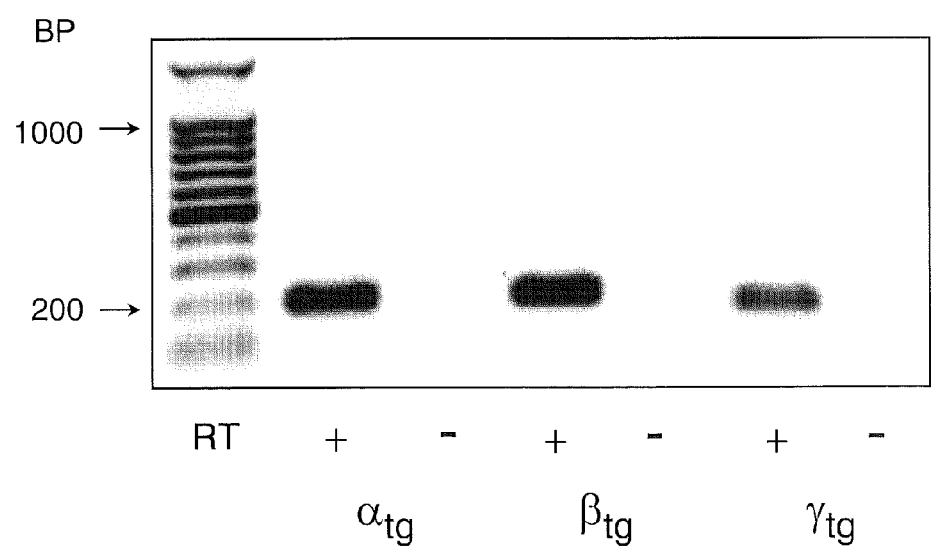
FIG. 4. Detection of expression of α, β and γ mENaC tg transcripts in mouse airways by RT-PCR from tracheal tissue.

The detection of expression of α, β and γ mENaC tg transcripts in mouse airways by RT-PCR from tracheal tissue is shown in FIG. 4. Expression of tg transcripts in tissue of tg positive mice was detected by amplification of PCR products of the expected size after reverse transcription of total RNA and using tg specific primer pairs.

Figure 5A:
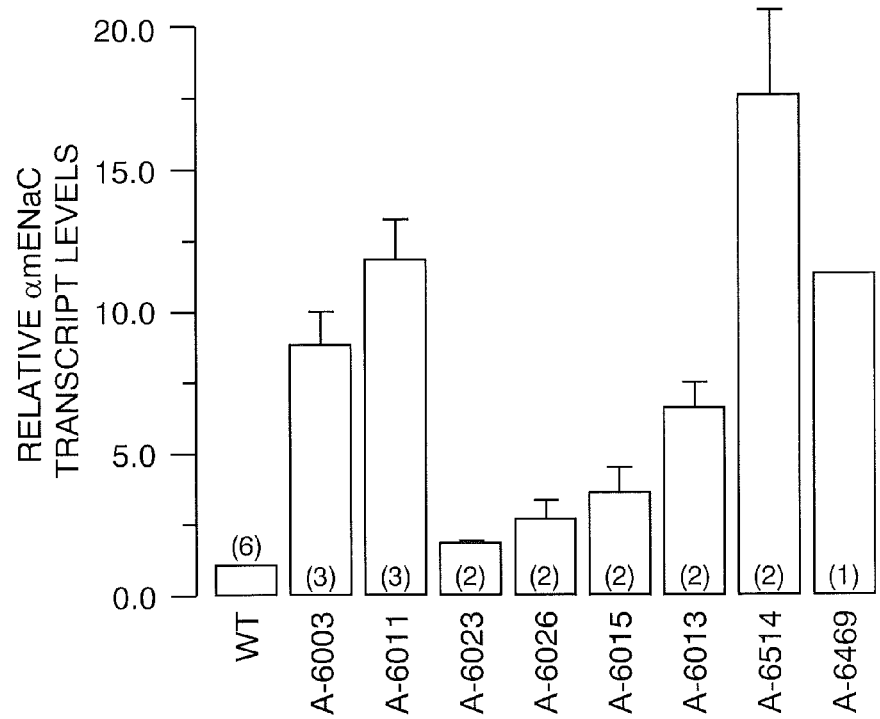
FIG. 5. Quantitation of expression levels of α(A), β(B), and γ mENaC (C) transgenes relative to WT in tracheal tissues of transgene positive mouse lines relative to wild type littermate controls, as determined by quantitative RT-PCR.
Figure 5B:
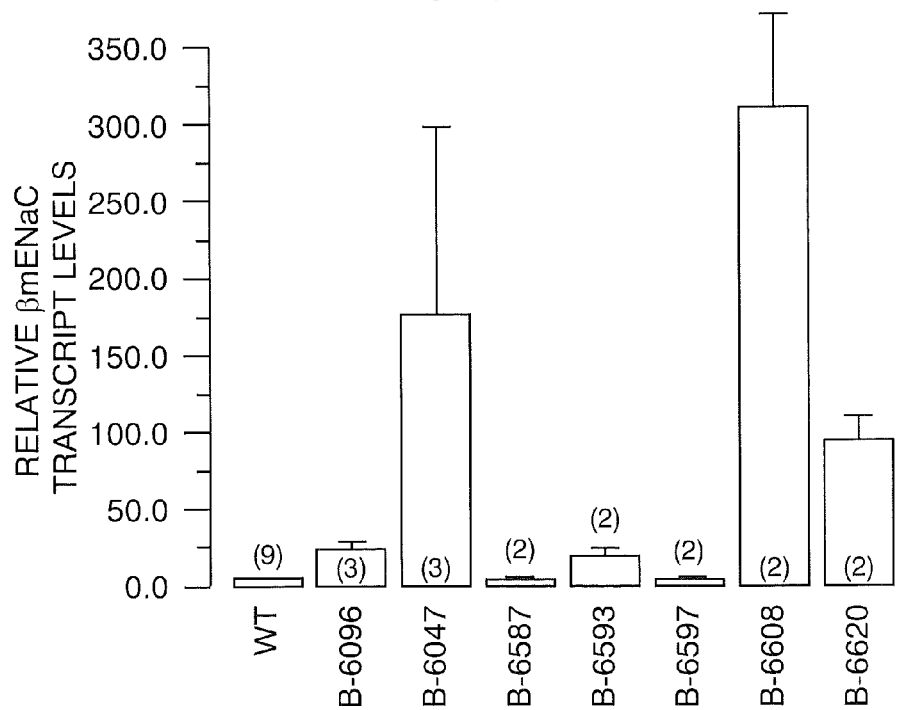
Figure 5C:
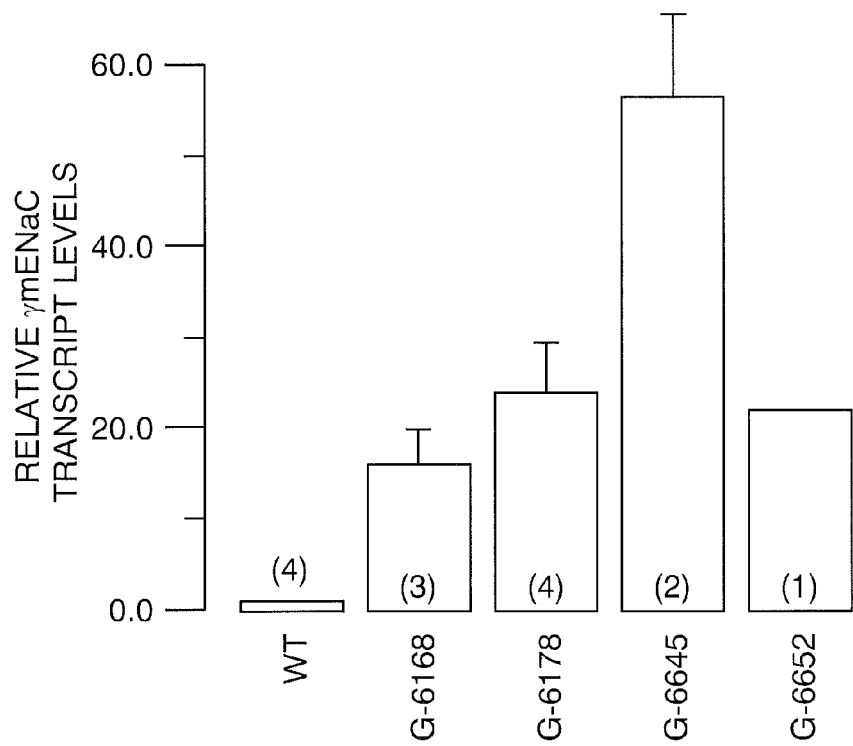

A quantitation of expression levels of α(A), β(B), and γ mENaC (C) transgenes relative to WT in tracheal tissues of transgene positive mouse lines relative to wild type littermate controls, as determined by quantitative RT-PCR is shown in FIG. 5.

EXAMPLE 3

Survival of Transgenic Mice

Figure 6A:
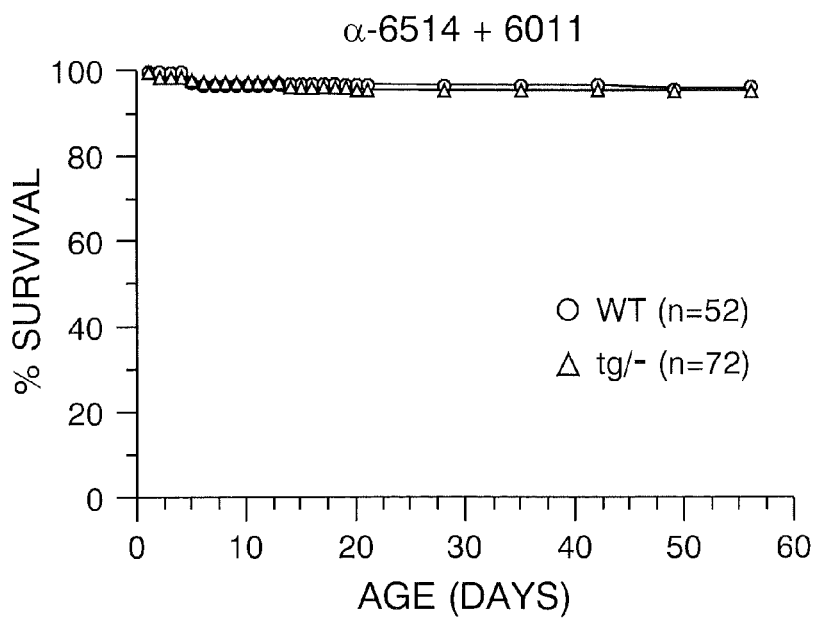
FIG. 6. Survival curves of α-, β- and γ-mENaC transgene positive (tg/−) mice and wild-type (−/−) littermate controls.
Figure 6B:
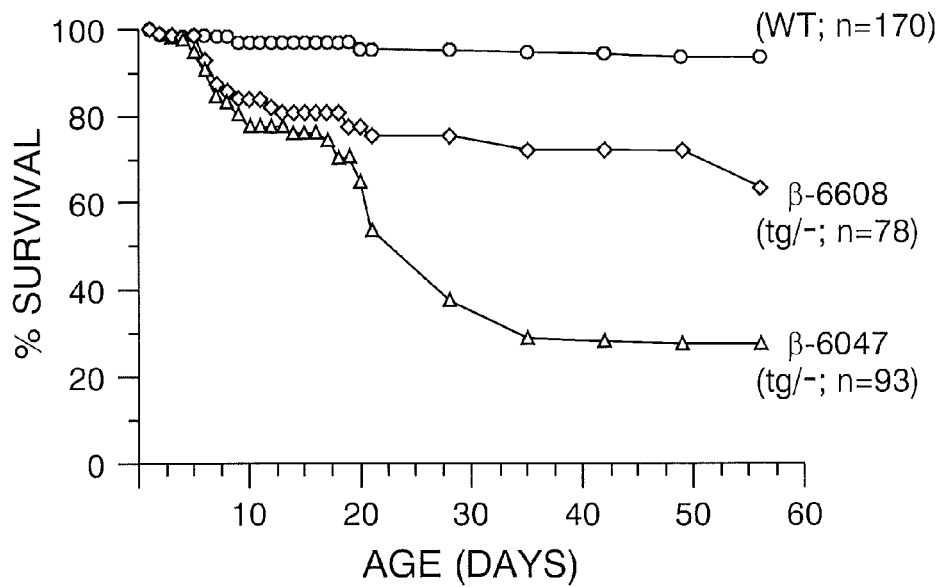
Figure 6C:
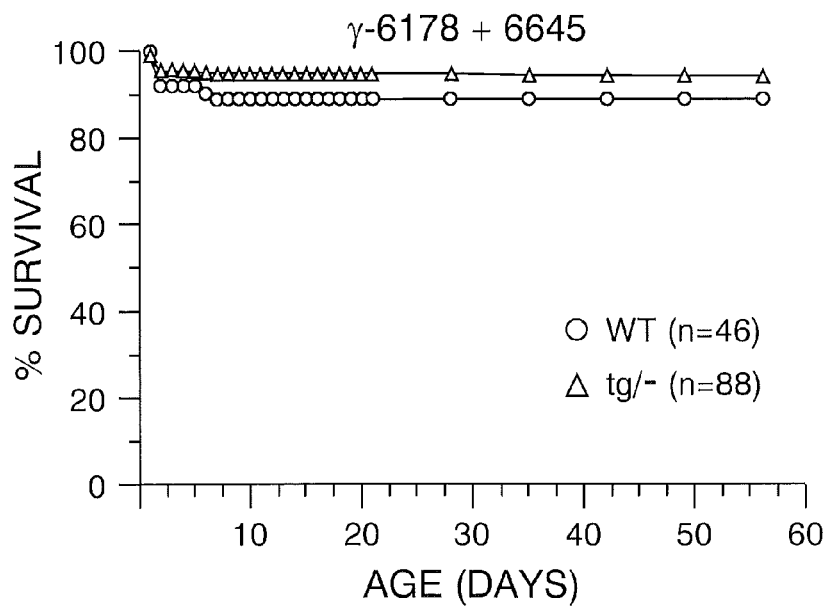

Survival curves of α-, β- and γ-mENaC transgene positive (tg/−) mice and wild-type (−/−) littermate controls are shown in FIG. 6. (A) α, (B) β, and (C) γENaC tg mice. All tg mice were heterozygous for the transgene.

EXAMPLE 4

Lung Histology from Transgenic Mice

Lung histology of a β mENaC transgene positive mouse that died spontaneously on day 20 is shown in FIG. 7. H&E staining shows occlusion of airways throughout the lung (a,c). AB-PAS staining identifies the intraluminal material as mucus. (b,d). Scale bars=200 mm.

Lung histology of βmENaC transgene positive mice that were euthanized at 3 (a,b) and 28 (c,d) days of age is shown in FIG. 8. Lung histology in βtg neonates is normal ($a_i$,$b_i$) with no evidence of mucus retention or goblet cell metaplasia ($a_{ii}$-$b_{ii}$). Older mice exhibit mucus retention with various degrees of airway obstruction, from narrowing of airways to complete plugging, and goblet cell metaplasia (GCM) ($c_i$, $d_{ii}$). H&E stain in ($a_i$,$b_i$,$c_i$,$d_i$) and AB-PAS in ($a_{ii}$,$b_{ii}$,$c_{ii}$,$d_{ii}$). All scale bars=200 mm.

Lung histology of a βtg mouse that was euthanized on day 28 is shown in FIG. 9. AB-PAS staining shows GCM along different regions of the bronchial tree, ranging from large airways to terminal bronchioles (AB-PAS). Scale bar=200 mm.

EXAMPLE 5

Functional Properties of Tracheal Tissue from Transgenic Mice

Figure 10A:
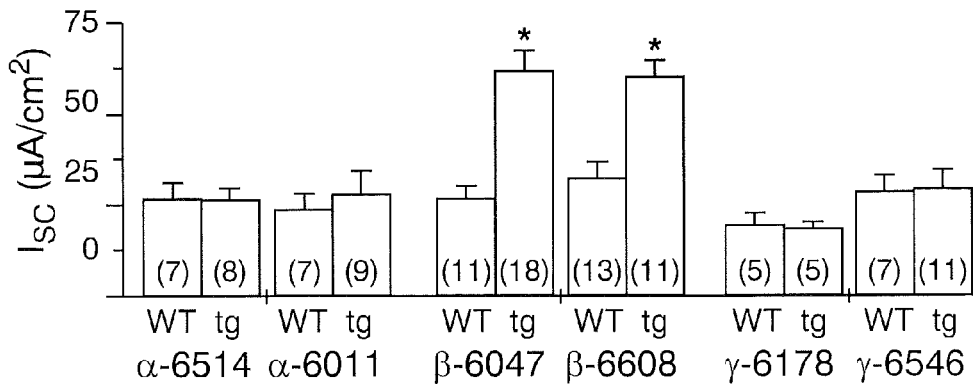
FIG. 10. Basal bioelectric properties of tracheal tissues of (A) neonatal (3-4 day old) and (B) adult (6 week old) αtg, βtg, and γtg ENaC over-expressing mice. *P<0.05 compared to WT. Data are means±SEM, n=3.
Figure 10B:
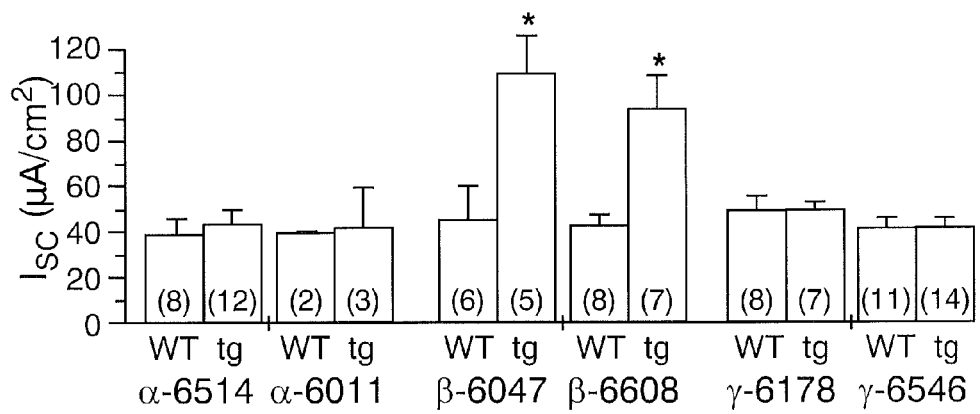

Basal bioelectric properties of tracheal tissues of (A) neonatal (3-4 day old) and (B) adult (6 week old) αtg, βtg, and γtg ENaC over-expressing mice are shown in FIG. 10. Electrogenic ion transport is significantly increased in βtg, but not in αtg or γtg mice. Two different transgenic founder lines were tested per transgene. *$P<0.05$ compared to WT. Data are means±SEM, n=3.

Figure 11A:
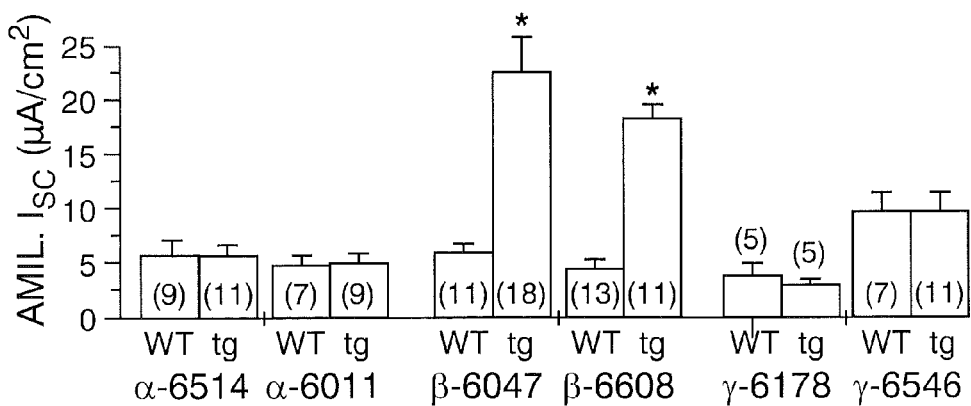
FIG. 11. Summary of amiloride-sensitive Isc in tracheal tissues of (A) neonate (3-4 days old) and (B) adult (6 week old) αtg, βtg, and γtg over-expressing mice. *P<0.05 compared to WT. Data are means±SEM, n=3.
Figure 11B:
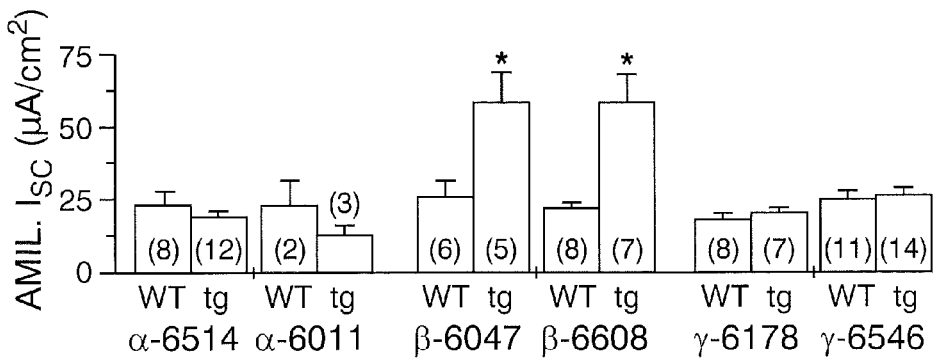

A summary of amiloride-sensitive Isc in tracheal tissues of (A) neonate (3-4 days old) and (B) adult (6 week old) αtg, βtg, and γtg over-expressing mice is shown in FIG. 11. Two different transgenic founder lines were tested per transgene. Electrogenic $Na^+$ transport is significantly increased in βtg, but not in αtg or γtg mice. *$P<0.05$ compared to WT. Data are means±SEM, n=3.

Figure 12A:
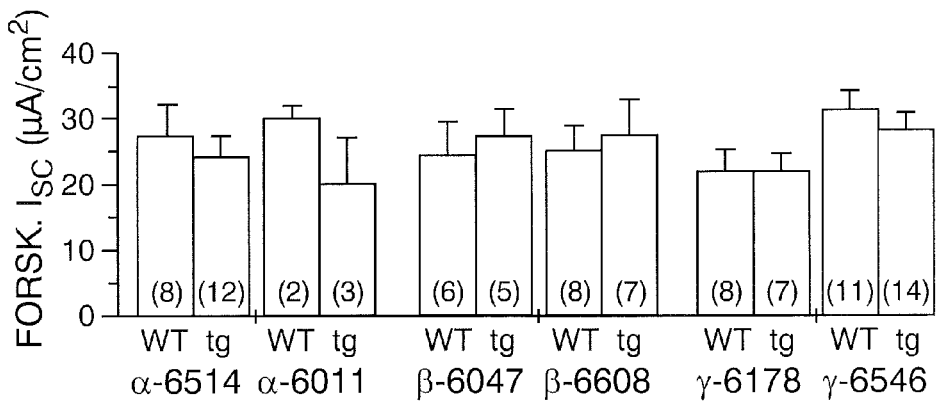
FIG. 12. Summary of (A) forskolin-induced Isc and (B) UTP-induced Isc in tracheal tissues of adult (6 week old) αtg, βtg, and ytg over-expressing mice. Data are means±SEM, n=3.
Figure 12B:
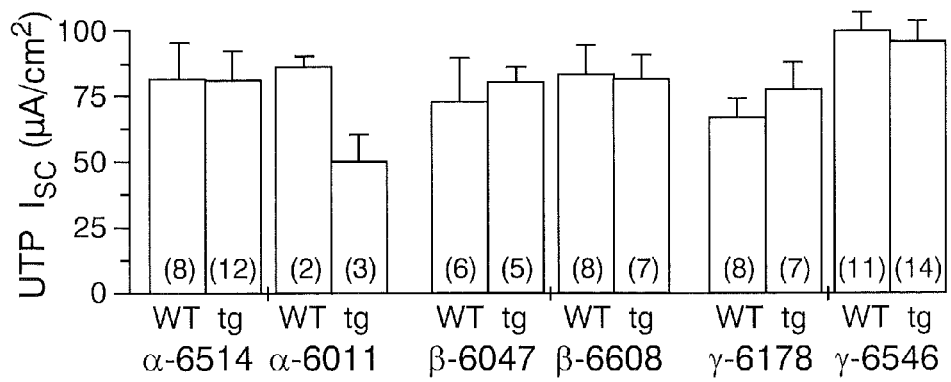

A summary of (A) forskolin-induced Isc and (B) UTP-induced Isc in tracheal tissues of adult (6 week old) αtg, βtg, and γtg over-expressing mice is given in FIG. 12. Experiments were performed in the presence of amiloride. Two different transgenic founder lines were tested per transgene. Forskolin- and/or UTP-induced Cl— secretion was not different in any of the transgenic lines. Data are means±SEM, n=3.

Figure 13A:
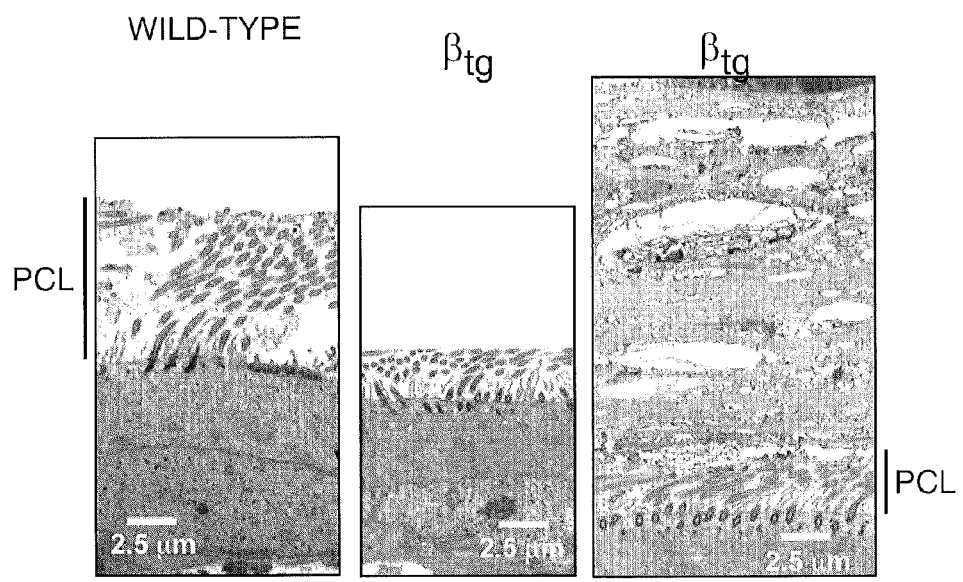
FIG. 13. Comparison of PCL height in OsO4/PFC fixed airways between β-mENaC over-expressing mice and WT littermate controls by TEM. (A) In WT animals the PCL is covered by a thin (0.3-0.4 mm) mucus film (electron dense epiphase). (B) Summary of PCL height in the trachea and bronchi of wild-type and btg over-expressing mice.
Figure 13B:
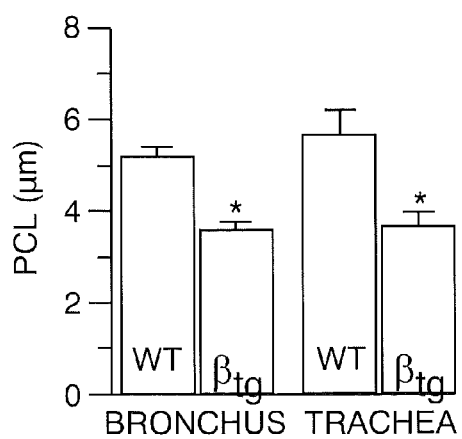

A comparison of PCL height in OsO4/PFC fixed airways between β-mENaC over-expressing mice and WT littermate controls by TEM is given in FIG. 13. (A)

In WT animals the PCL is covered by a thin (0.3-0.4 mm) mucus film (electron dense epiphase). Airways of βtg over-expressing mice show depletion of PCL, reduced PCL height and bending of cilia. Furthermore mucus accumulation is found in some airway regions of βtg mice, but not in WT. (B) Summary of PCL height in the trachea and bronchi of wild-type and btg over-expressing mice.

EXAMPLE 6

Mucus Clearance from Transgenic Mice

Figure 14:
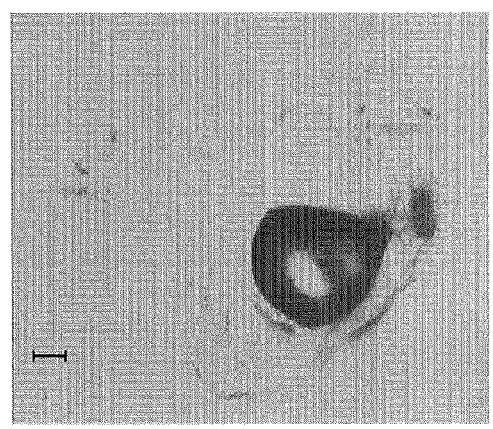
FIG. 14. Airway mucus cast removed from the trachea of a 5 day old β transgenic mouse pup. Scale bar=0.1 mm.

An airway mucus cast removed from the trachea of a 5 day old b transgenic mouse pup is shown in FIG. 14. An air bubble, the dark image, is clearly visible trapped within and distending the lumen of the cast. Scale bar=0.1 mm.

Figure 15:
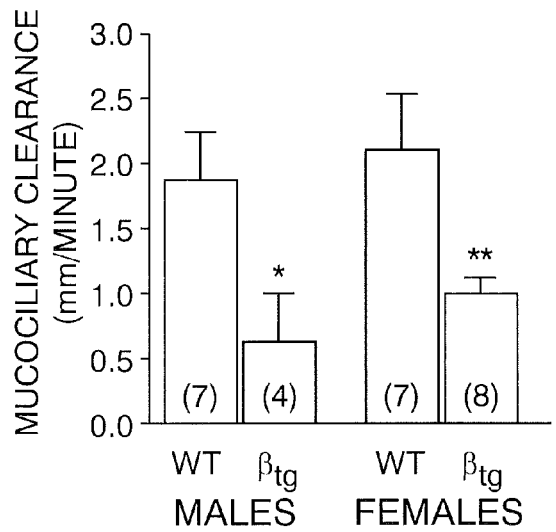
FIG. 15. Mucociliary clearance (MCC) in the lower airways of WT and β tg mice determined using in vivo microdialysis. Data shown are means±SEM, with the number of mice studied shown in parentheses. * p<0.03 compared to male WT, ** p<0.01 compared to female WT.

Mucociliary clearance (MCC) in the lower airways of WT and βtg mice as determined using in vivo microdialysis is shown in FIG. 15. Data shown are means±SEM, with the number of mice studied shown in parentheses. MCC is significantly reduced in β tg mice. * $p<0.03$ compared to male WT, ** $p<0.01$ compared to female WT.

EXAMPLE 7

Response of Transgenic Mice to Lung Bacterial Challenge

Histology (H&E and AB-PAS staining) on lungs from WT (panels A,C) and β tg (B,D) mice 72 hrs after nasal instillation of Pseudomonas (strain PAO1) is shown in FIG. 16. Intraluminal airway infection was detected in βtg mice (B,D), but not in WT mice (A,C). Airway infection in βtg mice was characterized by infiltration of mucus plugs/plaques with neutrophils and macrophages (B.D). No such lesions were detected in any of the WT mice (A,C). H&E stain (A,B) and AB-PAS (C,D). All scale bars=100 um.

Figure 17:
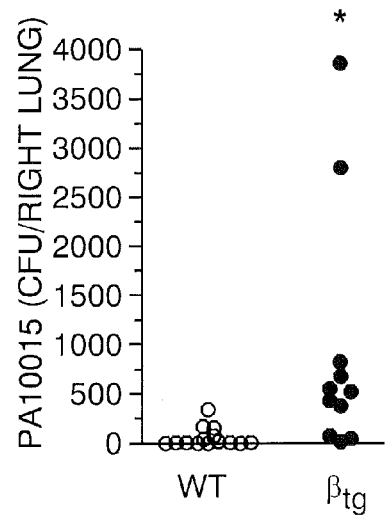
FIG. 17. Summary of quantitative bacteriology on lung homogenates from WT (open circles) and β tg (closed circles) mice after 72 hrs following challenge with *Pseudomonas aeruginosa* by tracheal instillation. * p<0.01 compared to WT.
Figure 16A:
FIG. 16. Histology (H&E and AB-PAS staining) on lungs from WT (panels A,C) and β tg (B,D) mice 72 hrs after nasal instillation of *Pseudomonas* (strain PAO1). All scale bars=100 um.
Figure 16C:
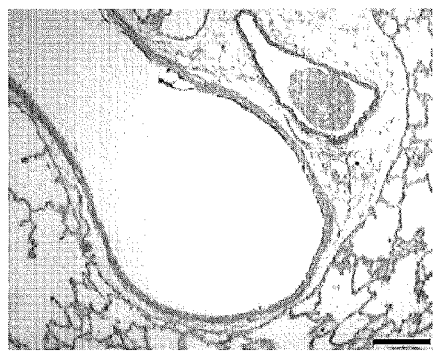
Figure 16B:
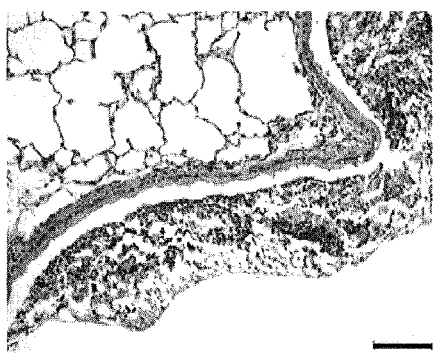
Figure 16D:
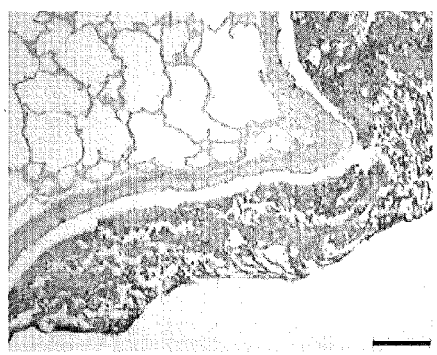

A summary of quantitative bacteriology on lung homogenates from WT (open circles) and βtg (closed circles) mice after 72 hrs following challenge with *Pseudomonas aeruginosa* by tracheal instillation is given in FIG. 17. Bacterial clearance was significantly reduced in b tg mice. * $p<0.01$ compared to WT.

The foregoing is illustrative of the present invention, and is not to be construed as limiting thereof. The invention is defined by the following claims, with equivalents of the claims to be included therein.

That which is claimed is:

1. A transgenic mouse whose genome comprises:
   i) a nucleic acid sequence encoding a human or mouse epithelial sodium channel (ENaC) β subunit operably linked to a mammalian lung epithelial cell promoter; and
   ii) a nucleic acid sequence encoding a human or mouse ENaC α subunit operably linked to a mammalian lung epithelial cell promoter,
   wherein said mouse expresses the human or mouse ENaC α and β subunits in lung epithelial cells, and wherein the mouse exhibits increased lung mucus plugging and airway inflammation and/or increased mortality as compared to the corresponding wild-type mouse.

2. The transgenic mouse of claim 1, wherein said promoter is selected from the group consisting of the Clara cell secretory protein (CCSP) promoter, the surfactant protein C promoter, the cytokeratin 18 promoter, and the human forkhead homologue 4 promoter.

3. The transgenic mouse of claim 1, wherein said mouse has increased lung mucus plugging and airway inflammation as compared to the corresponding wild- type mouse.

4. The transgenic mouse of claim 1, wherein said transgenic mouse has increased mortality as compared to the corresponding wild-type mouse.

5. The transgenic mouse of claim 1, wherein said transgenic mouse exhibits a cystic fibrosis or chronic obstructive pulmonary disease phenotype not exhibited by the corresponding wild-type mouse.

6. A transgenic mouse whose genome comprises:
   i) a nucleic acid sequence encoding a human or mouse epithelial sodium channel (ENaC) β subunit operably linked to a mammalian lung epithelial cell promoter; and
   ii) a nucleic acid sequence encoding a human or mouse ENaC γ subunit operably linked to a mammalian lung epithelial cell promoter,
   wherein said mouse expresses the human or mouse ENaC γ and β subunits in lung epithelial cells, and wherein the mouse exhibits increased lung mucus plugging and airway inflammation and/or increased mortality as compared to the corresponding wild-type mouse.

7. The transgenic mouse of claim 6, wherein said promoter is selected from the group consisting of the Clara cell secretory protein (CCSP) promoter, the surfactant protein C promoter, the cytokeratin 18 promoter, and the human forkhead homologue 4 promoter.

8. The transgenic mouse of claim 6, wherein said mouse has increased lung mucus plugging and airway inflammation as compared to the corresponding wild-type mouse.

9. The transgenic mouse of claim 6, wherein said transgenic mouse has increased mortality as compared to the corresponding wild-type mouse.

10. The nonhuman transgenic mouse of claim 6, wherein said transgenic mouse exhibits a cystic fibrosis or chronic obstructive pulmonary disease phenotype not exhibited by the corresponding wild-type mouse.

\* \* \* \* \*